United States Patent [19]

Cardis

[11] Patent Number: 4,770,800

[45] Date of Patent: Sep. 13, 1988

[54] REACTION PRODUCTS OF DIALKYL PHOSPHITES WITH ELEMENTAL SULFUR AND AN OLEFIN AND THEIR USE IN LUBRICANT COMPOSITIONS

[75] Inventor: Angeline B. Cardis, Florence, N.J.

[73] Assignee: Mobil Oil Corporation, New York, N.Y.

[21] Appl. No.: 139,354

[22] Filed: Dec. 30, 1987

Related U.S. Application Data

[63] Continuation-in-part of Ser. No. 883,665, Jul. 8, 1986, Pat. No. 4,717,491.

[51] Int. Cl.$^4$ .................................................. C10M 135/02
[52] U.S. Cl. ............................... 252/46.7; 252/32.7 E; 568/14
[58] Field of Search .................... 252/32.7 E, 46.7; 568/14

[56] References Cited

U.S. PATENT DOCUMENTS

| 2,862,016 | 11/1958 | Sallmann | 252/32.7 E |
|---|---|---|---|
| 3,192,162 | 6/1965 | Bartlett et al. | 252/46.6 |
| 3,984,448 | 10/1976 | Lippsmeier | 252/32.7 E |
| 4,152,275 | 5/1979 | Horodysky et al. | 252/46.6 |
| 4,207,195 | 6/1980 | Horodysky | 252/46.6 |
| 4,242,511 | 12/1980 | Grosse | 544/110 |
| 4,704,218 | 11/1987 | Horodysky | 282/46.6 |

Primary Examiner—Jacqueline V. Howard
Attorney, Agent, or Firm—Alexander J. McKillop; Michael G. Gilman; Van D. Harrison, Jr.

[57] ABSTRACT

Dialkyl phosphites are reacted with sulfur. The resulting product is further reacted with an olefin to form a lube oil product.

18 Claims, No Drawings

REACTION PRODUCTS OF DIALKYL PHOSPHITES WITH ELEMENTAL SULFUR AND AN OLEFIN AND THEIR USE IN LUBRICANT COMPOSITIONS

This is a continuation-in-part of copending application Ser. No. 883,665 filed July 8, 1986, now U.S. Pat. No. 4,717,491 which is incorporated herein by reference.

NATURE OF THE INVENTION

This invention relates to reaction products of dialkyl phosphites with elemental sulfur, reaction of the resulting product with epoxides, olefins, and amines, and use of these products in lubricating oil formulations.

PRIOR ART

U.S. Pat. No. 3,984,448 discloses the use of metal oxides, such as those of copper, calcium, barium, magnesium, zinc, cadmium, titanium or lead in conjunction with elemental sulfur and O,O-dialkylphosphorus acid esters to produce dialkyl thiophosphates.

U.S. Pat. No. 4,242,511 discloses the reaction of O,S-dialkylthiophosphoric acid esters by subjecting a thiophosphate to partial dealkylation in forming the salt of the dealkylated product by treatment with an amine.

Although dithiophosphate produces are known lubricant additives, their preparation involves processes resulting in noxious, undesirable by-products such as hydrogen sulfide and chloride-containing waste streams. Accordingly a primary object of this invention is to provide a process for preparing thiophosphate produces which eliminates the production of the aforementioned undesirable by-products.

SUMMARY OF THE INVENTION

In brief, this invention comprises in one aspect reacting dialkyl or trialkyl phosphites with elemental sulfur to provide an intermediate reactive product and then further reacting this intermediate product with epoxides, olefins, or amines to obtain a desired lube oil additive. In another aspect this invention comprises reacting the product thus obtained with phosphorus pentoxide to obtain a second improved lube oil additive. This invention also comprises a method for preparing lube oils wherein the aforedescribed additives are added to a selected lubricating oil. This invention further comprises the resulting lube oil product.

DESCRIPTION OF THE INVENTION

In the present invention an intermediate reaction product is obtained by reacting dialkyl phosphites of the general formula

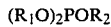

$(R_1O)_2POR_2$ where $R_1$ is a hydrocarbon radical of 4 to 18 carbon atoms and $R_2$ is hydrogen with elemental sulfur in the absence of any added catalyst in the presence of pulverulent sulfur at elevated temperature. Useful dialkyl phosphites include oleyl, phenyl, nonyl phenyl, octylphenyl, 2-ethyl hexyl, 1,3-dimethylbutyl, tridecyl, isodecyl, octyl and butyl, and mixed phosphites of the above radicals. If desirable, an unreactive organic solvent can be utilized. Preferably the organic solvent is selected from benzene, toluene, xylene, and mixed alkyl and aromatic petroleum distillates.

The pulverulent sulfur should conveniently have a mean particle size of less than one millimeter, preferably less than 0.01 millimeters, as this enables the reaction to be shortened. Reaction temperatures between 75° and 120° C. are preferred and a mole ratio of sulfur to phosphite of 0.8 to 1.2 is preferred. The reaction is carried out, preferably under a blanket of material such as nitrogen or other non-reactive gas. At the end of the reaction period the reaction mixture is allowed to cool to room temperature. The desired product is then stripped under vacuum to remove solvent and volatile byproducts and can be subsequently filtered or decanted from the reaction vessel.

This intermediate reaction product thus obtained is then further reacted with an amine, olefin, or alkaline oxide. The mole ratio of one of these reactants reacted with one mole of phosphite in the reaction product is 0.9 to 1.2. This second reaction is effected by mixing the reactants and allowing them to react (with added heat, if desirable) at a temperature between about 10° C. and about 90° C. The final product obtained can then be separated and purified by filtration and decantation. This product is then suitable for use in lube oil and grease formulations.

The amine compound to be reacted with the product formed by the alkyl phosphite and sulfur can be a primary, secondary or tertiary amine. Preferred amines include Primene 81R, benzotriazole, tolutriazole, amine-containing polymeric succinimides, and aromatic amines such as dialkyl diphenylamine and (alkylated) phenyl naphthylamines. Other amines which can be used include alkoxylated amines such as ethoxylated and propoxylated amines.

If olefins are to be utilized they can be selected from vinyl ethers, esters and amides and other such activated olefins.

Useful alkylene oxides include ethylene oxide and propylene oxide.

The resulting reaction products of this invention are used with lubricating oils or greases to the extent of from about 0.1% to about 10% by weight of the total composition. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodecene, etc. These thiophosphate esters are especially effective in synthetic oils formulated using mixtures of synthetic hydrocarbon olefin oligomers and lesser amounts of hydrocarbyl carboxylate ester fluids. The other synthetic oils, which can be used alone with the compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention in general aspects, the following examples are offered as specific illustrations. It is, of course, not intended to limit the types of olefins usable in this invention to those described in the following examples.

EXAMPLE 1

To 194 grams (1.0 mole) of dibutylhydrogen phosphite was added 32 grams (1.0 mole) of sulfur. The temperature was raised to 110° C. under a nitrogen atmosphere with stirring and held for eight hours.

The reaction mixture was cooled to ambient temperature and stirred under a nitrogen atmosphere as a solution of N-oleyl methacrylamide (330 grams, 0.98 moles) in 400 cc of toluene was added over a period of one-half hour. The temperature was increased to reflux and maintained for four hours. The solvent was distilled off and the product was vacuum topped at 20 mm Hg, 100° C.

The product was cooled to 50° C. and filtered through diatomaceous earth.

EXAMPLE 2

Following the procedure of Example 1 a product was prepared from dioleylhydrogen phosphite.

EXAMPLE 3

To 145 grams (0.25 moles) of dioleylhydrogenphosphite was added 8 grams (0.25 moles) of sulfur. The temperature was raised to 110° C. under a nitrogen atmosphere with stirring and held for eight hours.

The reaction mixture was cooled to ambient temperature and stirred under a nitrogen atmosphere as a solution of N,N-dicocomethacrylamide (114.5 grams, 0.25 moles) in toluene (100 cc) was added over one-half hour. The temperature was increased to reflux and held for four hours. The solvent was distilled off and the product was vacuum topped at 20 mm of Hg, 100° C. The product was cooled to 50° C. and filtered through diatomaceous earth.

EXAMPLE 4

Following the procedure of Example 3, a product was prepared from dibutyl hydrogen phosphite.

EXAMPLE 5

To 48.5 grams (0.25 moles) of dibutylhydrogen phosphite was added 8 grams (0.25 moles) of sulfur. The temperature was raised to 110° C. under a nitrogen atmosphere with stirring and maintained for 8 hours.

The reaction mixture was cooled to ambient temperature and stirred under nitrogen as a solution of N-t-alkyl methacrylamide (64.75 grams, 0.25 moles) in 100 cc of toluene was added over one-half hour. The temperature was increased to reflux and held for four hours.

The solvent was distilled off and the product was vacuum topped at 20 mm Hg, 100° C.

The product was cooled to 50° C. and filtered through diatomaceous earth.

EXAMPLE 6

Following the procedure of Example 5, a product was made from dioleylhydrogenphosphite.

EVALUATION OF PRODUCTS

The products described herein were blended in mineral oil and tested in the Shell Four-Ball Wear Test. The results in Table 1 demonstrate the antiwear protection afforded by these products.

TABLE 1

FOUR BALL WEAR TEST SCAR DIAMETER (MM)
½ Inch Balls, 52100 Steel, 60 Kg., 30 Minutes, 1.5%

| Example | Temp., °F. | 1000 RPM | 2000 RPM |
|---|---|---|---|
| Base Stock | 200 | 0.97 | 4.17 |
|  | 300 | 2.06 | 2.27 |
| 1 | 200 | 0.48 | 0.55 |
|  | 300 | 0.53 | 0.63 |
| 2 | 200 | 0.50 | 0.50 |
|  | 300 | 0.50 | 0.58 |
| 3 | 200 | 0.63 | 0.55 |
|  | 300 | 0.50 | 0.63 |
| 4 | 200 | 0.53 | 0.53 |
|  | 300 | 0.53 | 0.60 |
| 5 | 200 | 0.55 | 0.65 |
|  | 300 | 0.68 | 0.73 |
| 6 | 200 | 0.50 | 0.60 |
|  | 300 | 0.58 | 0.75 |

What is claimed is:

1. A process for making a reaction product suitable for use as an additive in lubricating oils comprising
   (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
   (b) separating the reaction product thereby obtained;
   (c) reacting the reaction product from (b) with an olefin in a mole ratio of olefin to phosphite of about 0.9 to about 1.2, at a temperature of between about 10° C. and about 90° C.; and
   (d) separating from the resulting reaction mixture the desired product.

2. The process of claim 1 wherein said phosphite has the structural formula $(R_1O)_2POR_2$ where $R_1$ is an alkyl hydrocarbon radical of 4 to 18 carbon atoms and $R_2$ is hydrogen.

3. The process of claim 1 wherein the dialkyl phosphite is selected from the group consisting of oleyl, phenyl, nonylphenyl, octylphenyl, 2-ethyl hexyl, 1,3-dimethyl butyl, tridecyl, isodecyl, octyl, butyl, and mixed phosphites.

4. The reaction product produced by the process of claim 1.

5. The reaction product produced by the process of claim 2.

6. The reaction product produced by the process of claim 3.

7. A lubricant composition comprising a lubricant and between about 0.1% and about 10% by weight of the total composition of the reaction product produced by the process of claim 1.

8. A lubricant composition comprising a lubricant and between about 0.1% and about 10% by weight of the total composition of the reaction product produced by the process of claim 2.

9. A lubricant composition comprising a lubricant and between about 0.1% and about 10% by weight of the total composition of the reaction product produced by the process of claim 3.

10. A process for making a reaction product suitable for use as an additive in lubricating oils comprising
  (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
  (b) reacting the reaction product from (a) with an olefin in a mole ratio of olefin to phosphite of about 0.9 to about 1.2, at a temperature of between about 10° C. and about 90° C.; and
  (c) separating from the resulting reaction mixture the desired product.

11. The process of claim 10 wherein said phosphite has the structural formula $(R_1O)_2POR_2$ where $R_1$ is an alkyl hydrocarbon radical of 4 to 18 carbon atoms and $R_2$ is hydrogen.

12. The process of claim 10 wherein the dialkyl phosphite is selected from the group consisting of oleyl, phenyl, nonylphenyl, octylphenyl, 2-ethyl hexyl, 1,3-dimethyl butyl, tridecyl, isodecyl, octyl, butyl, and mixed phosphites.

13. The reaction product produced by the process of claim 10.

14. The reaction product produced by the process of claim 11.

15. The reaction product produced by the process of claim 12.

16. A lubricant composition comprising a lubricant and between about 0.1% and about 10% by weight of the total composition of the reaction product produced by the process of claim 10.

17. A lubricant composition comprising a lubricant and between about 0.1% and about 10% by weight of the total composition of the reaction product produced by the process of claim 11.

18. A lubricant composition comprising a lubricant and between about 0.1% and about 10% by weight of the total composition of the reaction product produced by the process of claim 12.

* * * * *